United States Patent [19]

Knierim

[11] Patent Number: 4,764,111

[45] Date of Patent: Aug. 16, 1988

[54] REMINDER AND ENFORCER APPARATUS

[76] Inventor: Rupert W. Knierim, 6106 Top 'O Knox Dr., Knoxville, Tenn. 37918

[21] Appl. No.: 800,607

[22] Filed: Nov. 21, 1985

[51] Int. Cl.$^4$ ............................................. A61C 3/00
[52] U.S. Cl. ...................................... 433/5; 340/573; 340/309.15
[58] Field of Search ................ 433/5; 340/573, 309.15

[56] References Cited

U.S. PATENT DOCUMENTS

| | | | |
|---|---|---|---|
| 3,533,163 | 10/1970 | Kirschenbaum | 32/14 |
| 3,547,106 | 12/1970 | Bornmann | 340/573 |
| 3,885,310 | 5/1975 | Northcutt | 32/14 |
| 3,929,335 | 12/1975 | Malick | 340/573 |
| 3,982,238 | 9/1976 | Byers | 340/573 |
| 4,092,633 | 5/1978 | Fletcher et al. | 340/573 |
| 4,274,070 | 6/1981 | Thiene | 128/303.13 |
| 4,331,953 | 5/1982 | Blevins et al. | 340/573 |
| 4,392,122 | 7/1983 | Hocken | 340/309.15 |
| 4,524,243 | 6/1985 | Shapiro | 340/573 |

Primary Examiner—Kyle L. Howell
Assistant Examiner—Ruth S. Smith
Attorney, Agent, or Firm—Luedeka, Hodges & Neely

[57] ABSTRACT

An apparatus is disclosed for reminding a user of certain desired activity and for enforcing the performance of such activity. A clock generates clock pulses and a mechanism, such as a magnetic switch and magnet, is provided for detecting the performance of the desired activity and generating a detection signal when such activity is performed. A logic array is responsive to the clock pulses and the detection signal for selectively generating an electric alarm signal. In one form, the logic array is operable in response to the clock pulses to distinguish between at least two distinct time periods defined as an active time period and a dormant time period, and during the active time period, the logic array is operable to generate an electric alarm signal for a selected period of time in response to the absence of the detection signal. In the dormant period, the logic array will not generate the electric alarm signal regardless of the presence or absence of the detection signal. An alarm device, such as a beeper, is responsive to the alarm signal to generate an alarm that is perceivable by the user to indicate that the desired activity has not been performed. The alarm will continue for a sufficiently long period of time that it will irritate the user if he does not perform the activity that is desired. In one embodiment, the remainder is used to enforce the use of an orthodontic headgear. A magnet is mounted on the headgear and a magnetic switch is mounted in a mouthpiece which is fastened within the user's mouth. When the headgear is worn, the magnetic switch detects the presence of the magnet and will turn the alarm off during the active period.

14 Claims, 5 Drawing Sheets

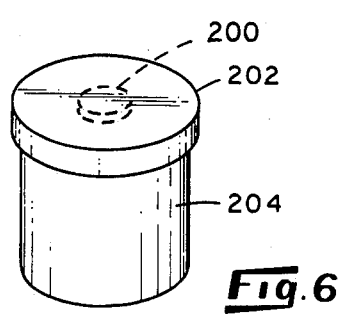
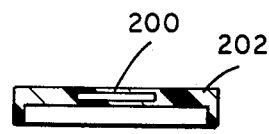
Fig. 6    Fig. 7
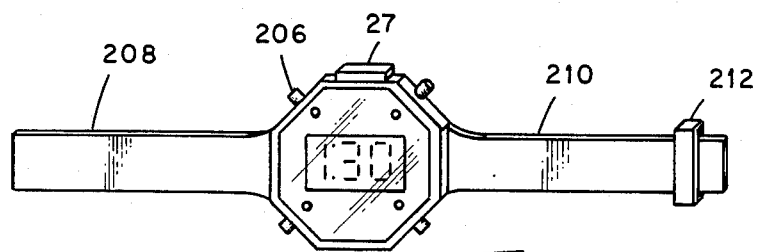
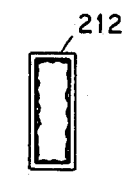
Fig. 8    Fig. 9
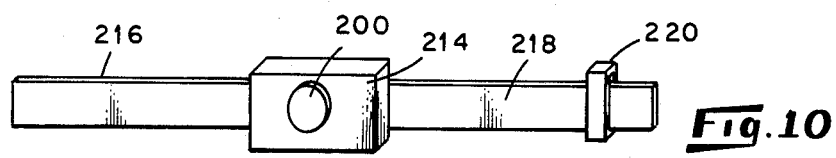
Fig. 10
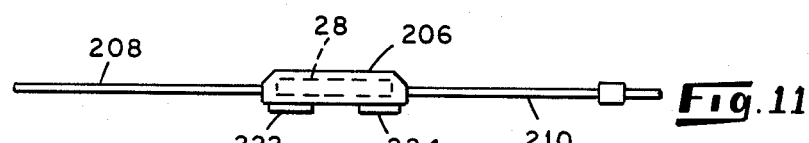
Fig. 11
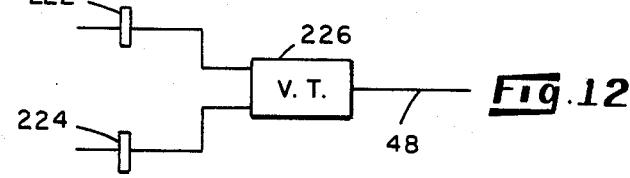
Fig. 12

REMINDER AND ENFORCER APPARATUS

FIELD OF INVENTION

The present invention relates to reminder systems and particularly relates to a reminder and enforcer system that generates an alarm that may be stopped by the user by the performance of a desired activity.

BACKGROUND AND SUMMARY OF THE INVENTION

The present invention reminds the user of the need to perform a desired activity and it enforces the performance of that activity by continuing to signal the user until the activity is performed. Numerous reminder systems, such as alarm clocks, are well known, but these reminder systems generally do not enforce a desired activity or even monitor the activity.

One form of the present invention is an orthodontic device for enforcing the use of an orthodontic headgear. The typical user of an orthodontic headgear is a teenager, and the headgear is usually used to move the patient's teeth rearwardly. Because of the awkwardness and discomfort of the headgear, teenagers are often uncooperative and will not use the headgear as ordered by the doctor.

Devices have been developed to enforce, or at least monitor, the use of orthodontic headgears. For example, U.S. Pat. No. 3,885,310 to Northcut discloses a timing system for an orthodontic headgear. In this system, the headgear includes a face bow that attaches to the patient's teeth and to a headstrap that fits behind the patient's head and pulls the bow toward the patient's face. A timer is built into the head strap that detects tension thereon and records the time that the strap is held in tension. This device assumes that the time of tensioning the head strap is equal to wearing time. However, an uncooperative patient could defeat this device by simply hanging the headgear over a door knob with weights attached to create the tension. Also, this device does not remind the patient or enforce the use of the headgear. It merely records the time of use in the hope of encouraging the patient to wear the device.

Another orthodontic monitoring device is disclosed in U.S. Pat. No. 3,533,163 to Kirschenbaum and this device also includes a face bow and a headstrap. A spring switch detects whether the strap is under appropriate tension and, if not, a radio transmitter mounted on the headgear transmits a signal to a remote receiver which sounds an alarm. Again, this device is easily defeated, such as by mounting the headgear on another object (a door knob), and there is no provision for reminding and enforcing.

In accordance with one form of the present invention, an orthodontic reminder and enforcer apparatus is provided for an orthodontic headgear. The headgear includes a conventional head strap with a modified face bow. The bow extends about the face and into the patient's mouth where it is attached to the teeth, and a magnet is preferably mounted on the front center of the bow. A mouthpiece is configured to fit within the mouth of the patient and is usually placed behind the front teeth. The mouthpiece includes a magnetic switch sealed within it and, when the face bow is in proper position on the teeth, the magnet on the face bow will be sufficiently close to actuate the magnetic switch in the mouthpiece.

A clock is mounted within the mouthpiece for generating clock pulses, and a logic circuit mounted within the mouthpiece is responsive to the clock pulses and the magnetic switch. The logic circuit counts the clock pulses and is capable of distinguishing between at least two distinct periods of time defined as a use period and a dormant period. During the use period, the logic circuit will generate an electric alarm signal if the magnetic switch is not actuated by the magnet. If the magnetic switch is actuated, the logic circuit interprets this condition as a detection signal indicating the presence of the magnet and the face bow, and it will cease generating the electric alarm signal. During the dormant period, the patient is not required to wear the headgear so the logic circuit will not generate the electric alarm signal regardless of whether the magnetic switch is actuated. An alarm, preferably a beeper, is mounted within the mouthpiece and generates a beep inside the patient's mouth in response to the electric alarm signal. During the use period when the magnetic switch is not actuated, the beeper will continue to beep for a sufficiently long time to irritate the patient and force him to wear the headgear. In other words, in order to turn off the beeper inside his mouth, the patient must wear the headgear. The beeping sound inside the patient's mouth is intended to be sufficiently irritating and, perhaps, embarassing, to cause the patient to prefer wearing the headgear over hearing a beeper inside his mouth.

The patient is not informed as to how or why the beeper system works, and the magnet on the face bow may be concealed on the face bow to appear as if it were part of a weld that normally is formed on the face bow. In fact, a patient may be misinformed as to how the device is working so that the patient's efforts, if any, to defeat the beeper system will be unsuccessful. For example, the patient could be told that the device detects the tension on the bow by way of a switch on the teeth to which the bow is attached. In this manner, the patient will try to defeat a nonexistant switch and tension detector system and, probably, will be unsuccessful.

The enforcer device of the present invention is not limited in its usefulness to orthodontic devices. For example, instead of mounting the magnet on a face bow, the magnet could be mounted in a medicine container. Whenever the beeper sounds, the magnet in the medicine container must be brought into close proximity with the mouthpiece to deactivate the beeper. Thus, to stop the beeper, the user must bring his medicine container to within inches of his mouth. Performing this activity will be sufficient to persuade most people to take their medicine. Having the reminder system built into one's mouth will prevent the patient from losing the beeper system and it will encourage him to not lose his medicine container. Devices in which a beeper system is built into a medicine container are often accidentally defeated by simply failing to carry the medicine container.

In accordance with another form of the present invention, the apparatus is contained within a main housing and straps are provided for permanently attaching the main housing to the person. For example, the main housing may be attached to a person's arm by means of straps that are secured together by a deformable clamp so that the straps may be released only by cutting them. A magnetic switch is mounted within the main housing for switching and generating a detection signal in response to the presence of a magnet in near proximity to the magnet switch. A magnet is mounted on another part of the body or in another desired location. When the main housing is brought to within a predetermined distance of the magnet, the magnetic switch will be actuated. A clock is mounted within the housing and produces clock pulses. A logic device is responsive to the clock pulses and the detection signal for selectively generating an alarm signal, and the logic device is operable to begin generating the electric alarm signal at predetermined times and to continue generating the electric alarm signal until at least one detection signal is generated by the magnetic switch. An alarm, such as a beeper, is responsive to the electric alarm signal to produce an alarm perceivable by the person. In this construction, an alarm will be generated at selected times and will continue to be generated until the magnet is placed in near proximity to the magnetic switch.

In this form of the invention, the main housing may be mounted on one part of a patient's body and the magnet may be mounted on another part of the body. The desired activity in this case is to have the patient move his body so that the magnet and the main housing will come together. For example, if it were desired to have the patient touch his knee with his elbow, the magnet could be mounted on the knee and the main housing mounted near the elbow. Also, either the magnet or the main housing could be mounted in a location remote from the patient. For example, if it were desired to have the patient lift his knee to a desired height, the main housing could be mounted on the patient's knee and the magnet could be mounted on the wall at a desired height.

Thus, when the alarm signal was generated, the patient would be reminded to go to the wall and lift his leg to a desired height. It will be appreciated that the logic device may be modified to generate the electric alarm signal at a variety of different times and under a variety of different circumstances according to the activity that is desired. Also, the action necessary to deactivate the alarm could be varied. For example, the logic device could require ten separate "on" and "off" signals from the magnetic switch in order to deactivate the beeper. In this mode, for example, a patient may be required to lift the main housing on his knee to a magnet mounted on a wall for a selected number of times in order to generate the appropriate number of "on" and "off" signals that are required to stop the alarm.

BRIEF DESCRIPTION OF THE DRAWINGS

The present invention may best be understood by reference to a Detailed Description of several embodiments thereof when considered in conjunction with the Drawings in which:

FIGS. 6 and 7 show a medicine container with a magnet molded into the cap of the container;

FIG. 8 discloses a main housing for mounting the reminder and enforcing apparatus of the present invention on a patient's limb;

FIG. 9 discloses a deformable metal clamp that is used to secure together the straps shown in FIG. 8;

FIG. 10 discloses a magnet mounted on a strap system for being attached to a patient's limb;

FIG. 11 shows an alternate embodiment of the present invention in which the main housing of the reminder and enforcer apparatus is mounted on a patient's limb with electrodes formed on the bottom of the main housing for contacting the patient's skin; and FIG. 12 discloses a schematic diagram of electrodes and a voltage detection circuit.

DETAILED DESCRIPTION

Figure 1:
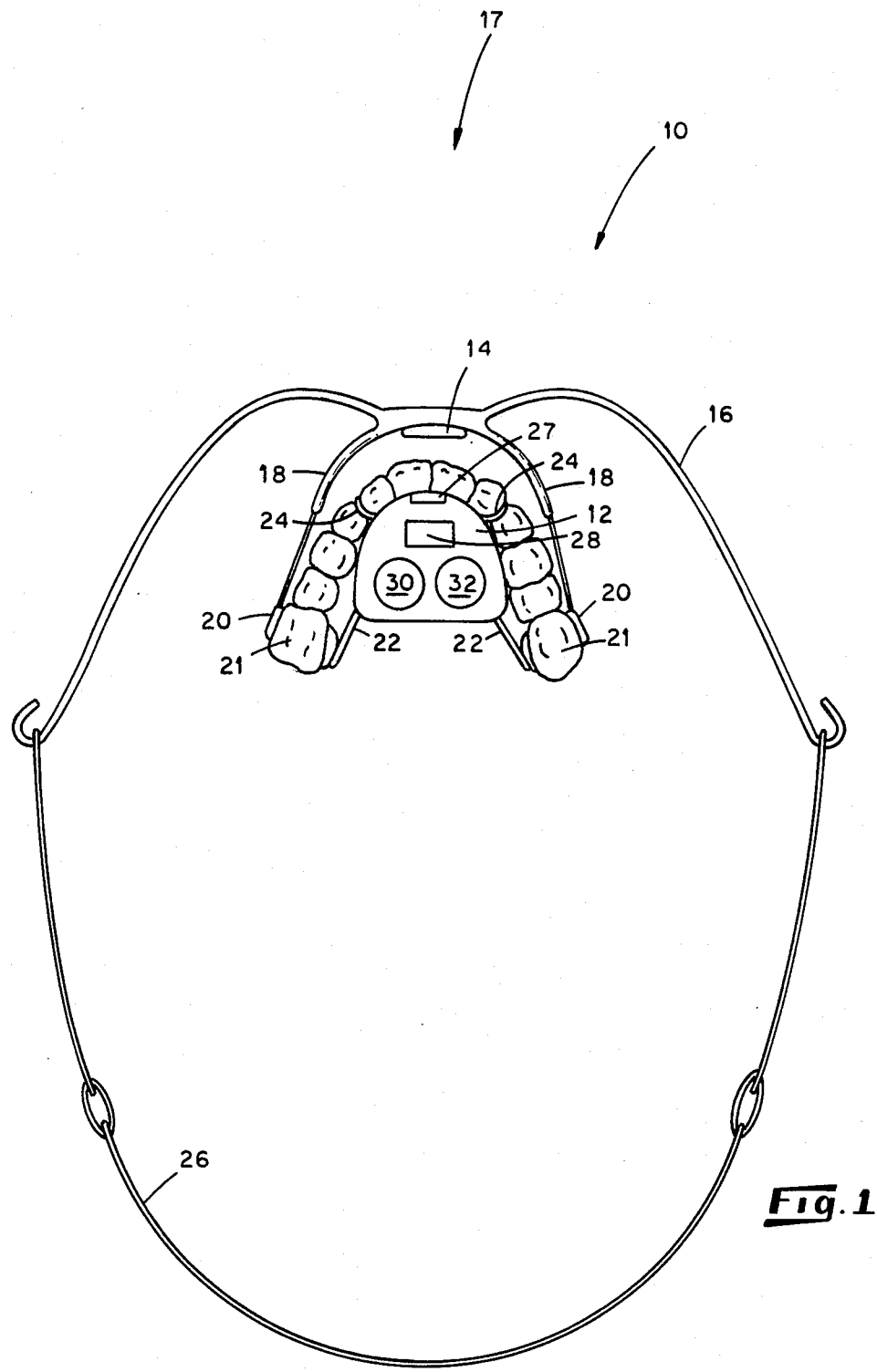
FIG. 1 is a perspective view of an orthodontic headgear mounted on a patient's teeth with a mouthpiece mounted within the patient's mouth next to the front teeth.

Referring now to the drawings in which like reference characters designate like or corresponding parts throughout the several views, there is shown in FIG. 1 a reminder and enforcer apparatus 10 that includes a mouthpiece 12 which is mounted within a patient's mouth and a magnet 14 which is mounted on a face bow 16 that will be positioned immediately outside of the patient's mouth. The face bow 16 is a part of an orthodontic headgear 17 which also includes a pair of prongs 18 that extend into and within a patient's mouth and are mounted on the patient's teeth 21 by means of metal mounts 20. A pair of rear mounting wires 22 extend forwardly from the teeth 21 of the patient and hold the rear of the mouthpiece 12 within the patient's mouth. A pair of front mounting wires 24 are attached between the front of the mouthpiece 12 and the front teeth of the patient. This could be part of a pressure activated switch to allow enforcement of wearing orthodontic elastics.

When the bow 16 and prongs 18 are positioned as shown in FIG. 1, a headstrap 26 extends around and behind the patient's head and places tension on the bow 16 to place a force on teeth 21 and, in this position, the bow 16 will place the magnet 14 in close proximity to the mouthpiece 12. The mouthpiece 12 includes a magnetic switch 27, a logic circuit 28, a battery 30 and a beeper speaker 32, all encapsulated within a plastic material such as methyl methacryate that is commonly used in the field of orthodontics for appliances supported within the mouth of a patient. Preferably, the mouthpiece 12 is specially constructed in the lab to fit within a particular patient's mouth.

As shown in FIG. 1, the magnetic switch 27 is placed in the front portion of the mouthpiece 12 so that it will be as close as possible to the front of the patient's mouth and the magnet 14 mounted on the face bow 16. The strength of the magnet 14 and the sensitivity of the magnetic switch 27 are selected so that the switch 27 will be easily activated whenever the prongs 18 are mounted on the mounts 20. Thus, the magnet 14 and switch 27 are chosen so that the switch 27 will be activated whenever the magnet 14 comes within a predetermined distance, about one inch, of the switch 27. The signal for the magnetic switch 27 is received by the logic circuit 28 and in accordance with the logic built into the circuit, it will sound the beeper speaker 32 in the event that the patient is not wearing the face bow 16 during a period of time when he should. Both the beeper speaker 32 and the logic circuit 28 are powered by a battery 30 which is also encapsulated within the mouthpiece 12. It will be understood that the mouthpiece 12 may be used with many different orthodontic devices. For example, it could be used to detect whether orthodontic elastics are being worn. In such case pressure switches would be mounted on the teeth in substitution for the magnetic switch 27. The elastics would mount onto the pressure switches and would switch them on, and the mouthpiece 12 would sound an alarm if the elastics were not worn during selected time periods.

Figure 2:
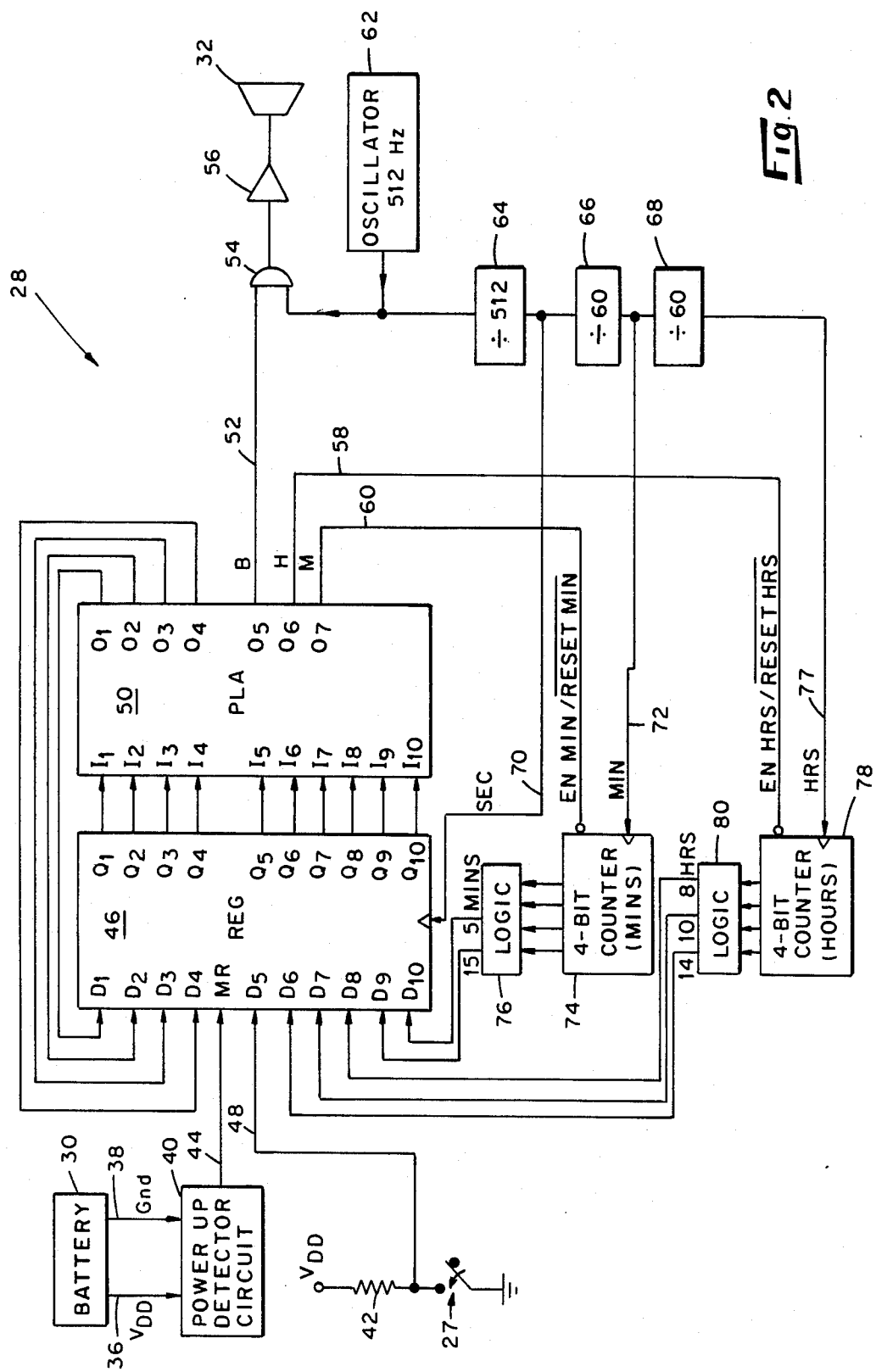
FIG. 2 is a diagram of the circuitry used for the reminder and enforcer of the present invention.

The circuit diagram shown in FIG. 2 illustrates in more detail the construction of the logic circuit 28 which is preferably implemented as an integrated circuit but it may also be implemented with discrete elements or by using a single chip device like the Motorola MC 146805 and coding its ready only memory. The logic circuit 28 is powered by a battery 30 whose output is applied through lines 36 and 38 to a power up detector circuit 40. The detector circuit 40 detects when a battery 30 is placed into the device and generates a pulse on line 44 in response thereto.

The magnetic switch 27 is connected on one side to ground and on the other side to a resistor 42 which is connected to the battery. Line 48 is also connected between the resistor 42 and the magnetic switch 27. When the switch 27 is open, the voltage of the battery 30 ($V_{dd}$) appears on line 48. When the magnetic switch 27 is closed, the voltage on line 48 drops to zero indicating the detection of the magnet 14.

Both lines 44 and 48 are attached to inputs of a register 46. Line 44 is connected to input MR which is the master reset of register 46. When the battery 30 is placed in the circuit, the power-up detector 40 issues a pulse on line 44 to the input MR (master reset) of the register 46 and this action causes all zeros to be issued from the register as address zero for a programmed logic array 50.

The inputs to register 46 are $D_1$ through $D_{10}$ and input MR. The outputs of register 46 and $Q_1$ through $Q_{10}$ and these outputs are connected to the inputs $I_1$ through $I_{10}$ of the programmed logic array 50. The outputs of the programmed logic array 50 are labeled $O_1$ through $O_7$. Outputs $O_1$ through $O_4$ of the array 50 are connected to inputs $D_1$ through $D_4$, respectively, of register 46. Output $O_5$ of the array 50 is applied through line 52 to an AND gate 54 whose output is applied through an amplifier 56 to the beeper speaker 32. The output $O_6$ is an hours reset output that is applied to line 58 and the output $O_7$ is a minutes reset signal that is applied to line 60.

An oscillator 62 provides a 512 hertz signal that is applied to one of the inputs of AND gate 54 and to a divider 64 that divides the frequency by 512. The output of the divider 64 is applied through line 70 to the register 46 as a clock signal indicating seconds and is applied to a divider 66 that divides the frequency by 60. The output of the divider 66 indicates minutes and is applied to a minute counter 74, and the output of the counter 74 is connected through a logic circuit 76 to indicate the passage of five minutes and fifteen minutes. A timed-out signal is applied from the logic circuit 76 to input $D_{10}$ to indicate that five minutes has timed out since counter 74 was reset, and a signal is applied to input $D_9$ to indicate that fifteen minutes has timed out. When a pulse appears on line 60, the counter 74 is reset to zero.

The output of the divider 66 is also applied to a divider 68 that divides by sixty and provides pulses on line 77 indicating hours to the hours counter 78. The output of the counter 78 is applied through a logic circuit 80 to indicate the passage of a certain number of hours. A signal is supplied to input $D_8$ of register 46 to indicate that eight hours has timed out since counter 78 was reset; a pulse to input $D_7$ indicates that then hours has timed out and a pulse to input $D_6$ indicates that fourteen hours has timed out. A pulse on line 58 to counter 78 resets the counter 78 to zero.

Figure 3:
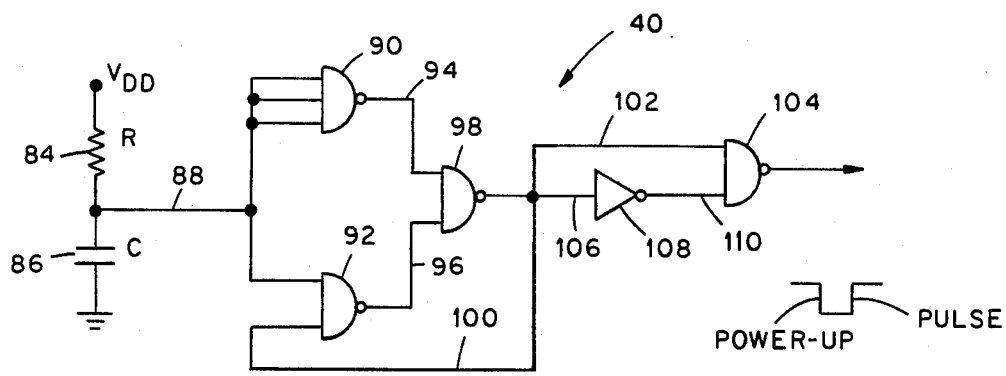
FIG. 3 is a power-up detection circuit used in the circuit of FIG. 2 for the purpose of detecting when a battery is inserted within the circuitry.

The components shown in FIG. 2 are conventional with the possible exception of the power up detection circuit 40 which is shown in FIG. 3. The circuit 40 includes a resistor 84 in series with a capacitor 86 connected to the battery 30 ($V_{dd}$ and ground). An input line 88 is connected between the resistor 84 and capacitor 86 and provides all of the inputs to NAND gate 90 and one of the inputs to NAND gate 92. The output of NAND gate 90 is applied through line 94 to one of the inputs of NAND gate 98, and the output of NAND gate 92 is applied through line 96 to the other input to NAND gate 98. The output of NAND gate 98 is applied through a feedback loop 100 to the other input of NAND gate 92, through line 102 to one of the inputs of a NAND gate 104 and through line 106 to an inverter 108 whose output is applied through line 110 as the other input to NAND gate 104.

When the battery 30 is inserted into the circuit, the voltage on line 88 is initially zero or ground. As the capacitor 86 charges, the voltage on line 88 increases exponentially until it is equal to the voltage of the battery ($V_{dd}$). The output of the NAND gate 104 is initially high. When the battery is inserted, and the voltage on line 88 begins to rise, the output of NAND gate 104 goes low until the capacitor 86 is full charged and then it goes high again. Thus, a pulse is generated at the output of NAND gate 104 to indicate the connection of the battery.

Figure 4:
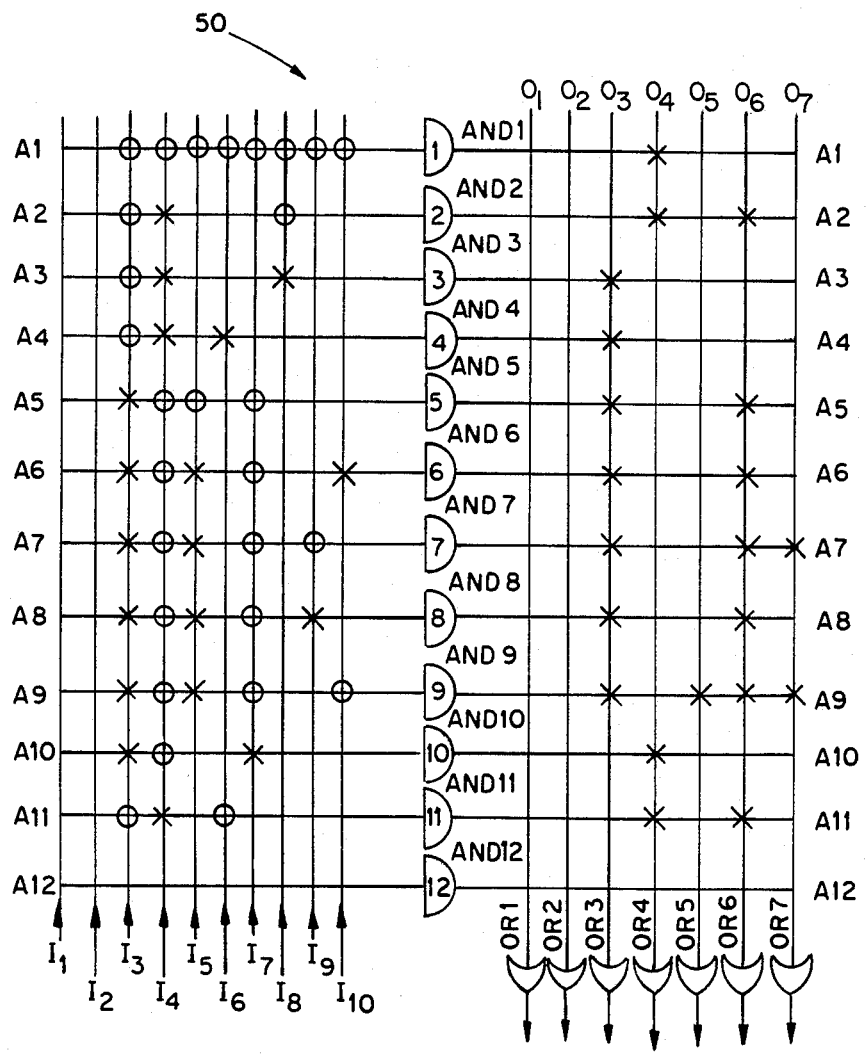
FIG. 4 is a circuit diagram of a programmed logic array used in the apparatus of the present invention and shown in FIG. 2.

Referring now to FIG. 4, there is shown a diagram illustrating the logic of the programmed logic array 50. The inputs to the programmed logic array shown in FIG. 4 are labeled $I_1$ through $I_{10}$ and they correspond to the inputs labeled $I_1$ through $I_{10}$ as shown in FIG. 2. The inputs $I_1$ through $I_{10}$ as shown as vertical lines in FIG. 4 that intersect with twelve horizontal lines labeled A1 through A12. The horizontal lines A1 through A12 represent the inputs to twelve AND gates that are labeled AND 1 through AND 12. Each of the AND gates shown in FIG. 4 actually have ten inputs and each of the lines A1 through A12 are representative of those ten inputs. For example, the ten inputs to AND 1 is represented by the line A1. The intersections of the input lines $I_1$ through $I_{10}$ and the horizontal lines A1 through A12 are indicative of the inputs to the AND gates AND 1 through AND 12. If an "X" appears at the intersection of two lines, that particular input is applied directly to the AND gate. If a "0" appears at the intersection, the inverted input is applied to the AND gate. IF neither a "0" or a "X" appear at the intersection, then the logic circuit "doesn't care" about the particular input and it is always high. For example, the input $I_1$ and $I_2$ are not used in this embodiment and neither "X's" nor "0's" appear at the intersections of $I_1$ and $I_2$ with the lines A1 through A12.

Referring to the top left-hand side of FIG. 4, it will be appreciated that on line A1 all of the inputs to the gate AND 1 are inverted. Thus, when inputs $I_3$ through $I_{10}$ are low, all of the inputs to gate AND 1 go high and the output of gate AND 1 goes high. Referring to line A2, it will be appreciated that the three inputs to the gate AND 2 are $I_3$, $I_4$ and $I_8$. Since $I_3$ and $I_8$ are inverted, the gate AND 2 will go high when $I_3$ is low, $I_8$ is low and $I_4$ is high. In like manner, gate AND 3 goes high when $I_8$ is high, $I_4$ is high, and $I_3$ is low. AND 4 goes high when $I_6$ and $I_4$ are high and $I_3$ is low. AND 5 goes high when $I_7$, $I_5$ and $I_4$ are low and $I_3$ is high.

AND 6 goes high when $I_{10}$, $I_5$ and $I_3$ go high and $I_7$ and $I_4$ are low. AND 7 goes high when $I_5$ and $I_3$ are high and $I_9$, $I_7$ and $I_4$ are low. AND 8 goes high when $I_9$, $I_5$ and $I_3$ are high and $I_7$ and $I_4$ are low. AND 9 goes high when $I_5$ and $I_3$ are high and $I_{10}$, $I_7$ and $I_4$ are low. AND 10 goes high when $I_7$ and $I_3$ are high and $I_4$ is low. AND 11 goes high when $I_6$ and $I_3$ go low and $I_4$ goes high. AND 12 is not used.

Referring to the right side of FIG. 4, the vertical lines are labeled $O_1$ through $O_7$ and they correspond to $O_1$ through $O_7$ shown on FIG. 2. The horizontal lines are again labeled A1 through A12. At the intersections of the horizontal lines A1 through A12 and the vertical lines $O_1$ through $O_7$ and "X" indicates a true input to the OR gates OR 1 through OR 7 and the absence of an "X" indicates a "no connection" situation. The lines $O_1$ through $O_7$ are connected through OR gates OR1 through OR7. Each of the vertical lines above the OR gates is representative of twelve inputs to the OR gate OR1 through OR7. That is, each OR gate has twelve inputs. OR1 and OR2 are not used. The gate OR3 will go high whenever any one of the gates AND 3 through AND 9 go high. Gate OR4 will go high when one of gates AND 1, AND 2, AND 10 or AND 11 go high. OR5 will go high when gate AND 9 goes high. Gate OR6 will go high when one of gates AND 2, AND 5, AND 6, AND 7, AND 8, AND 9 or AND 11 go high. Gate OR7 will go high when gates A7 or A9 go high.

Figure 5:
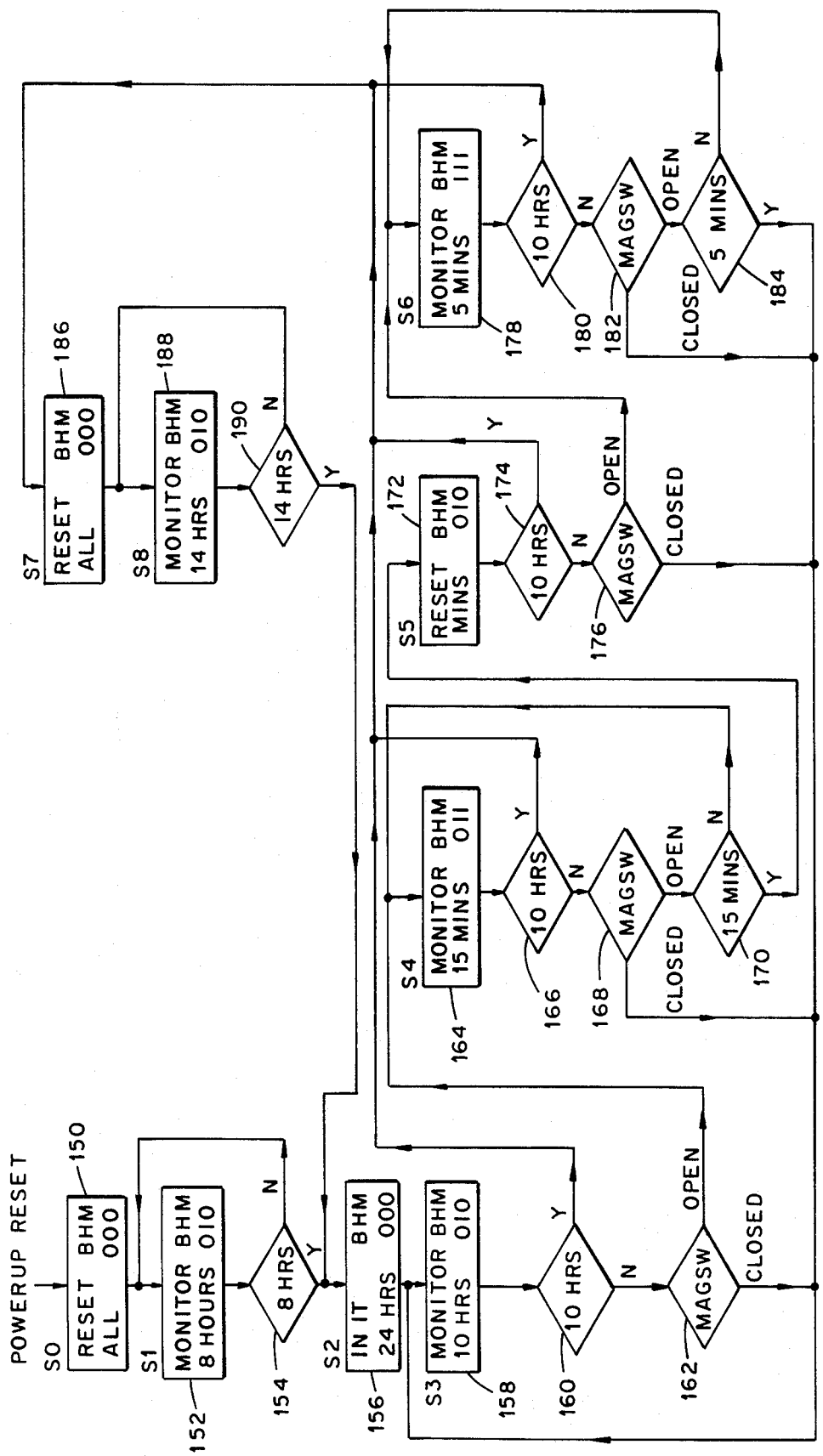
FIG. 5 is a flow chart of the operation of the circuitry of FIG. 2.

The operation of the logic circuit 28 and the programmed logic array 50 may be best understood by reference to the flow chart set forth in FIG. 5. Referring to FIGS. 2, 4 and 5, the operation begins when the battery 30 is inserted into the system and the power-up circuit 40 places a pulse on line 44 to the input MR of register 46. At this point in time, all zeros are issued from the register as address zero for the array 50. A reset is performed by placing a pulse on output $O_6$ and $O_7$ of the array 50 which are applied to reset counters 78 and 74. Also, the output $O_5$ applied to line 52 goes low to disable the speaker 32. Referring to blocks 152 and 154 of the flow chart in FIG. 5, the logic circuit 28 begins to monitor time. After eight hours has timed out by the counter 78 since a reset, circuit 80 applies a signel to input $D_8$ of the register 46 and input $I_8$ goes high. When this occurs, pulses are again applied at the outputs $O_6$ and $O_7$ to reset counters 78 and 74 and the system begins a 24-hour cycle as indicated by block 156 in FIG. 5. The eight hour time period is typically timed out only once in the life of the apparatus 10. The purpose of the eight hour time cycle is to allow the orthodontist to insert the battery 30 into the circuit 28 at 1:00 p.m. and, thus, initialize the 24-hour cycle to begin at 9:00 p.m. that night.

As indicated by block 158 in FIG. 5, the circuit 28 will now monitor the hour counter 78 to determine whether ten hours has passed since the counters were reset. If ten hours has not passed, as indicated by block 62, the logic will inquire as to whether the magnetic switch 27 is closed. If the signal on line 48 which is applied to the register input $D_5$ indicates that the magnetic switch 27 is closed, then the system will continue monitoring for ten hours. If the magnetic switch 27 is open, the logic will move to block 164 and will begin to monitor the minute counter 74 to determine whether fifteen minutes has passed. As indicated by blocks 166, 168 and 170, if the ten hours period has not timed out, if the magnetic switch 27 is still open, and if fifteen minutes times out, the logic circuit 28 moves to block 172 and a pulse is generated on output $O_7$, line 60, to reset the minute counter 74. As indicated by block 174 and 176, if the ten hour period has still not timed out and the magnetic switch 27 is still open, the logic moves to block 178. At this point, the output $O_5$ applied on line 52 goes high and the beeper speaker 32 begins to sound an alarm. As indicated by blocks 180, 182 and 184, so long as the ten hour peiod has not passed, the magnetic switch 27 remains open, and five minutes has not passed since the counter 74 was initialized (reset), the beeper speaker 32 will continue to sound. The patient may stop the beeper speaker 32 from sounding by bringing the magnet 14 within close proximity of the magnetic switch 27 so as to close the magnetic switch 27. Thus, the patient is forced to wear the face bow 16 in order to prevent the beeper speaker 32 from sounding. As indicated by block 182, if the magnetic switch is closed, the logic will return to block 158. If the patient replaces the face bow 16 and then removes it immediately, the logic will again move to block 164 and wait fifteen minutes. If the face bow 16 and magnet 14 are not placed in proper position within that fifteen minute period, the logic will move to the blocks 172 and 178 and begin beeping for five minutes.

Referring to block 184, if the patient does not replace the face bow 16 and magnet 14 in its proper position so as to close the magnetic switch 27, the beeper will stop beeping after five minutes and return to logic block 158. From logic block 158, assuming the magnetic switch is still open, the circuit 28 will move to logic block 164, will time out fifteen minutes, will move to the logic blocks 172 and 178 and will again start the beeping for another five minute period or until the magnetic switch 27 is closed. Referring to logic block 162, as long as the magnetic switch stays closed during the ten hour period, the logic circuit 28 will continue to monitor and will not sound the beeper through speakers 32.

Recalling that the orthodontist installed the battery at 1:00 p.m. and that the ten hour period began at 9:00 p.m., the ten hour period monitored at logic block 158 will time out at 7:00 a.m. in the morning. When this occurs, the logic circuit 80 will apply a signal to input $D_7$ of register 46 which will apply an input to $I_7$ of the programmed logic array 50. When an input appears at input $I_7$, the hour counter 78 and the minute counter 74 are reset and zero and circuit 28 begins a fourteen hour monitoring period as indicated by logic blocks 186, 188 and 190 in FIG. 5. So long as the fourteen hour period has not timed out, circuit 28 will continue monitoring the counter 78, but it will not generate the beeping sound until the fourteen hour period has passed. After the fourteen hour period has timed out, a signal is applied from the logic circuit 80 to inut $D_6$ of register 46 which applies an input signal to input $I_6$ of the programmed logic array 50. When this signal occurs on input $I_6$ the logic circuit 28 resets both the hour counter 78 and the minute counter 74 to zero and begins the ten hour monitoring period again as indicated by blocks 156 and 158 in FIG. 5. Since the fourteen hour period began at 7:00 a.m., it will time out at 9:00 p.m. Thus, this particular device is designed to remind and enforce the use of the orthodontic headgear only during the time period from 9:00 p.m. to 7:00 a.m. Of course, by slightly modifying the logic of the programmed logic array 50 and by providing different counters 78 and 74, the circuit 28 could be modified to beep at different times during the day and for different periods of time according to the desired application.

As described above, the reminding and enforcing apparatus 10 is used to remind and enforce the use of an orthodontic appliance. However, this apparatus could have other applications. For example, as shown in FIG. 6, a magnet 200 could be embedded in a cap 202 for a medicine container 204. In this embodiment, the logic array 50 is modified to remind and enforce every eight hours so that the user is urged to take his medicine every eight hours. In this embodiment, only the eight hour line of counter 78 is monitored, and when eight hours times out a signal is applied to input $D_8$ of register 46 which is then applied to input $I_8$ of array 50. In response, array 50 resets counters 78 and 74 and begins monitoring counter 74. After the eight hour timed out signal is received at input $D_7$, the array 50 will begin the fifteen minute rest/five minute alarm cycle until the magnetic switch 27 is closed. This cycled is the same as previously described in conjunction with FIG. 5. After the switch 27 is closed, the beeper speaker 32 will cease sounding until another eight hour timed out signal appears at input $D_8$. When the apparatus 10 of the present invention is used to remind a patient to take medicine, it will be necessary to implant the device in the mouth of the patient only in extreme cases. Usually, it would be preferred to permanently mount the device on the patient's arm. For that purpose, there is shown in FIG. 8 a housing 206 that resembles a wrist watch for containing the circuit shown in FIG. 2. In this embodiment, the magnetic switch 27 is mounted on the exterior of the housing 206 to insure that it is easily switched. The housing 206 has straps 208 and 210 extending from it and it may be mounted on a patient's arm in a fashion similar to that of a wrist watch. A deformable metal clamp 212 is used to clamp the straps 208 and 210 together on the patient's arm so that the housing 206 may not be removed easily. This clamping system is frequently used in hospitals to secure name bands on patients' and any number of these conventional systems may be incorporated into the apparatus as illustrated in FIG. 8.

Likewise, a housing 214 may be used to mount a magnet 200 on a patient's limb or other part of his body. Straps 216 and 218 are attached to the housing 214 and a metal clamp 220 is used to secure the straps 216 and 218 together in a permanent fashion. The only way the straps 216 and 218 may be separated and the device removed from the patient is to break the straps. Using the devices illustrated in FIGS. 8 and 10, a magnet 200 could be mounted to a patient's ankle or knee and the circuit 28 could be mounted in a housing 206 and attached above a patient's elbow. In this arrangement, the patient would be forced to touch his elbow to either his knee or his ankle in order to stop the beeping, and the logic array 50 could be modified to monitor the number of times the elbow touched the knee or ankle. In this manner, physical activity required for physical therapy could be reminded and enforced.

Referring now to FIG. 11, there is shown yet another alternate embodiment of the present invention which is similar to the embodiment shown in FIG. 8 except that it includes electrodes 222 and 224 mounted on the back of the main housing 206 so that they contact the skin of a person wearing the apparatus. The logic circuit 28 is modified as shown in FIG. 12 in that the magnetic switch 27 is deleted and, instead, the two electrodes 222 and 224 and the voltage threshold detector 226 is inserted therefor. The electrodes 222 and 224 are connected to the voltage threshold detector 226 which simply monitors the voltage level between the two electrodes. When any voltage is detected above a predetermined threshold voltage, an output is applied from the circuit 226 through line 48 to the register 46. The embodiment illustrated in FIGS. 11 and 12 is designed for use in monitoring the physical activity of a pariticular muscle of a patient. For example, if a patient's physical therapy calls for the exercise of a thigh muscle, the apparatus of FIG. 11 would be secured to the thigh directly above the muscle which should be exercised. When it is time to exercise the muscle, a reminder beep will sound. When the muscle is exercised, the electrical activity of the muscle increases and it may be detected through the electrodes 222 and 224. The threshold voltage of the voltage threshold detector circuit 226 is adjusted so that when the muscle is being exercised, the threshold will be exceeded and a signal will be applied to the register 46 through line 48. The precise logic involved for the monitoring, reminding and enforcing may vary with individual applications, but, for example, the logic array 50 may be modified to remind the patient to exercise twice a day and it will require that the exercise be performed for a total of at least fifteen minutes or the beeper will begin sounding. That is, the voltage detected by the circuit 226 must exceed the predetermined threshold for a period of fifteen minutes or the beeper will continue sounding.

Although particular embodiments of the present invention have been described in the foregoing Detailed Description, it will be understood that the invention is capable of numerous rearrangements, modifications or substitutions of parts without departing from the scope of the invention as defined by the appended claims. In particular, it will be appreciated that the logic array 50 could be modified to perform a great variety of monitoring, reminding and enforcing regimens. Also, the particular physical activity required to satisfy the enforcing regimen could be varied. The physical activity could require certain movement of the body, the present of a bottle cap, the presence of a orthodontic headgear, the presence of physical activity in a particular muscle, or any number of other physical activities.

What is claimed is:

1. An activity reminder and enforcer apparatus for reminding a user of certain desired activity and for enforcing the performance of such activity, comprising:
   a power source;
   clock means powered by said power source for generating clock pulses;
   first and second objects that must be brought into proximity during the desired activity;
   means for detecting the performance of the desired activity and for generating a detection signal when the activity is performed; said means for detecting having a sensor mechanism mounted in said first object and having a signal producing means mounted in said second object, said sensor mechanism being operable to sense the signal produced in said second object when said first and second objects are brought into proximity, one to the other, and to generate the detection signal when said proximity is sensed.
   logic means responsive to the clock pulses and the detection signal for selectively generating an electric alarm signal, said logic means being operable in response to the clock pulse and, independently of the detection signal, to distinguish between at least two distinct time periods defined as an active time period and a dormant time period, said dormant time period being of a sufficient duration, on the order of hours, that a user may forget to perform the desired activity, said logic means being operable during the active time period to generate the electric alarm signal for a selected period of time in response to the absence of the detection signal and being operable during the dormant time period to not generate the electric alarm signal regardless of the absence of the detection signal; and signaling means responsive to the electric alarm signal to generate a signal for the selected period of time perceivable by the user to indicate that the desired activity has not been performed.

2. The apparatus of claim 1
wherein said signal producing means comprises:
a magnet mounted in the second object; and
wherein said sensor mechanism comprises:
magnetic switch means mounted in the first object for generating a detection signal when said magnet is brought to within a predetermined distance of said magnetic switch means.

3. The apparatus of claim 1 wherein said means for detecting further comprises:
a medicine container;
wherein said signal producing means comprises:
a magnet mounted on the medicine container; and
wherein said sensor mechanism comprises:
magnetic switch means for generating a detection signal when said magnet is brought to within a predetermined distance of said magnetic switch means.

4. The apparatus of claim 1 further comprising alarm signal repeating means operable during the active period in the absence of an input signal to repetively generate said alarm signal, said alarm signal repeating means being operable to alternately generate said electric alarm signal for a predetermined alarm period and not generate said electric alarm signal for a predetermined rest period.

5. The apparatus of claim 1 wherein said signal producing means comprises:
a pair of electrodes dimensioned and configured to fit against the skin of a user; and
wherein said sensor mechanism comprises:
voltage detector means connected to the electrodes for detecting the voltage therebetween and for generating the detection signal when the voltage on said electrode exceeds a predetermined threshold.

6. An activity reminder and enforcer apparatus for reminding a user of certain desired activity and for enforcing the performance of such activity, comprising:
a power source;
clock means powered by said power source for generating clock pulses;
means for detecting the performance of the desired activity and for generating a detection signal when the activity is performed;
logic means responsive to the clock pulses and the detection signal for selectively generating an electric alarm signal, said logic means being operable in response to the clock pulses to distinguish between at least two distinct time periods defined as an active time period and a dormant time period, said logic means being operable during the active time period to generate the electric alarm signal for a selected period of time in response to the absence of the detection signal and being operable during the dormant time period to not generate the electric alarm signal regardless of the absence of the detection signal;

signaling means responsive to the electric alarm signal to generate a signal for the selected period of time perceivable by the user to indicate that the desired activity has not been performed;
said means for detecting comprising:
an orthodontic headgear;
a magnet mounted on said orthodontic headgear;
magnetic switch means for generating a detection signal when said magnet and headgear are moved to a position within a predetermined distance of said magnetic switch means; and
means for mounting said magnetic switch means within the mouth of the user whereby said magnetic switch means will be actuated when the user wears the headgear.

7. An orthodontic apparatus for reminding a patient to wear an orthodontic device that attaches to the patient's teeth and for enforcing the user of the orthodontic device during a selected period of time defined as a use period, comprising:
a mouthpiece configured to fit within the patient's mouth and being attached therein;
means for detecting the presence of an orthodontic device when attached to the patient's teeth and for generating a detection signal;
a battery mounted within said mouthpiece;
clock means mounted within said mouthpiece and powered by said battery for generating clock pulses;
logic means mounted within said mouthpiece and responsive to the clock pulses and the detection signal for selectively generating an electric alarm signal, said logic means being operable in response to the clock pulses to distinguish between at least two time periods defined as a use period and a dormant period, said logic means being operable during the use period to generate the electric alarm signal in response to the absence of the detection signal, said logic means being operable during the dormant period to not generate the electric alarm signal regardless of the absence of the detection signal; and
an alarm device mounted within said mouthpiece for generating an alarm perceivable by the patient in response to the electric alarm signal to remind the patient to wear the orthodontic device and being operable to continue generating the alarm for a selected period of time sufficient to enforce the wearing of the orthodontic device.

8. The apparatus of claim 7 wherein said means for detecting comprises:
a magnet mounted on said orthodontic device in a position for being disposed in near proximity to said mouthpiece when the device is attached to the patient's teeth; and
magnetic switch means mounted within said mouthpiece for switching and generating the detection signal in response to the presence of a magnet in near proximity to the magnetic switch means, the position of said magnet on the orthodontic device and the location of said mouthpiece being selected so that when the device is attached to the teeth, said magnet will be positioned sufficiently near said mouthpiece to switch said magnetic switch means.

9. The apparatus of claim 7 wherein said logic means further comprises means for repetitively generating the electric alarm signal for an alarm period of a predetermined length of time and for not generating said electric alarm signal during a rest period of a predetermined length of time, said rest period occurring after said alarm period and said alarm period being of a sufficient time that the alarm will irritate the patient and enforce the wearing of the orthodontic device.

10. The apparatus of claim 7 further comprising;
a power up circuit means for detecting the insertion of the battery into the mouthpiece and for generating a power up signal; and
said logic means further comprising initialization means responsive to said power up signal and said clock pulses to time out an initialization period of a selected time period and then, after the initialization period, to activate said logic means to begin alternately timing out the use period and the dormant period with each use period being followed by a dormant period and each dormant period being followed by a use period.

11. The apparatus of claim 7 wherein said logic means comprises a programmed logic array;
a timing circuit means for counting said clock pulses, for generating a use period time out signal after counting a first predetermined number of clock pulses, and for generating a dormant period time out signal after counting a second predetermined number of clock pulses;
said programmed logic array being responsive to said dormant period time out signal to reset said timing circuitry to zero and to generate said electric alarm signal in response to the absence of the detection signal; and
said programmed logic array being responsive to said use period time out signal to reset said timing circuitry to zero and to not generate the electric alarm signal regardless of the absence of the detection signal.

12. An apparatus for reminding a person to perform a desired activity and for enforcing the performance of the activity, comprising:

a magnet mounted on a support means;
a main housing;
means for attaching said main housing to a person;
magnetic switch means mounted within said main housing for switching and generating a detection signal in response to the presence of the magnet in near proximity to said magnetic switch means;
a power source mounted within said housing;
clock means mounted within said main housing and powered by said power source for generating clock pulses;
logic means responsive to the clock pulses and the detection signal for selectively generating an electric alarm signal, said logic means being operable, in response to the clock pulses and independently of the detection signal, to distinguish between at least two distinct time periods defined as an active time period and a dormant time period, said dormant time period being of a sufficient duration, on the order of hours, that a user may forget to perform the desired activity, said logic means being operable only during the active time period to begin generating an electric alarm signal at predetermined times and to continue generating said electric alarm signal until at least one detection signal is generated by said magnetic switch means and being operable only during the dormant time period not to generate the electric alarm signal regardless of the absence of the detection signal; and
alarm means responsive to said electric alarm signal to produce an alarm perceivable by the person whereby an alarm will be generated at selected times and will continue until said magnet is placed in near proximity to said magnetic switch means.

13. The apparatus of claim 12 wherein said support means comprises: means for attaching the magnet to the body of the person whereby the person must move his body in a desired movement to place the magnet in near proximity to the main housing which is also attached to the person.

14. The apparatus of claim 12 wherein said support means comprises: a medicine container having said magnet attached thereto whereby the person must bring said medicine container to a position of near proximity to said magnetic switch means at selected times in order to stop the generation of the alarm.

* * * * *

UNITED STATES PATENT AND TRADEMARK OFFICE
CERTIFICATE OF CORRECTION

PATENT NO. : 4,764,111
DATED : August 16, 1988
INVENTOR(S) : Rupert W. Knierim

It is certified that error appears in the above-identified patent and that said Letters Patent is hereby corrected as shown below:

In the Abstract, line 22, delete "remainder" and insert --reminder--.

Column 5, line 14, delete "ready" and insert --read--.

Column 6, line 3, delete "then" and insert --ten--.

Column 6, line 8, delete "detection" and insert --detector--.

Column 6, line 31, delete "full" and insert --fully--.

Column 6, line 54, delete "IF" and insert --If--.

Column 7, line 47, delete "signel" and insert --signal--.

Column 7, line 62, delete "62" and insert --162--.

Column 8, line 50, delete "and" and insert --to--.

Column 9, line 21, delete "cycled" and insert --cycle--.
Column 10, lines 43 and 44, delete "present" and insert --presence--.
Column 12, Claim 7, line 26, delete "user" and insert --use--.
Column 13, Claim 10, line 14, after comprising delete ";" and insert --:--.

Signed and Sealed this

Thirty-first Day of January, 1989

Attest:

DONALD J. QUIGG

*Attesting Officer*     *Commissioner of Patents and Trademarks*